United States Patent
Muraki

(10) Patent No.: US 6,822,015 B2
(45) Date of Patent: Nov. 23, 2004

(54) RUBBER COMPOSITION USED FOR A RUBBER STOPPER FOR A MEDICAMENT OR FOR A MEDICAL TREATMENT OR ITS CROSSLINKED PRODUCT

(75) Inventor: Tomoyasu Muraki, Tokyo (JP)

(73) Assignee: Daikyo Seiko, Ltd., Tokyo (JP)

( * ) Notice: Subject to any disclaimer, the term of this patent is extended or adjusted under 35 U.S.C. 154(b) by 0 days.

(21) Appl. No.: 10/058,737

(22) Filed: Jan. 30, 2002

(65) Prior Publication Data

US 2003/0100696 A1 May 29, 2003

(30) Foreign Application Priority Data

Jan. 30, 2001 (JP) ........................................ 2001-021455

(51) Int. Cl.$^7$ ................................................ C08F 2/46
(52) U.S. Cl. .................. 522/157; 522/150; 522/153; 522/154; 522/155; 522/158; 522/159; 522/165; 522/160; 264/494; 264/496
(58) Field of Search ................................ 522/150, 155, 522/157, 158, 159, 160; 264/494, 496

(56) References Cited

U.S. PATENT DOCUMENTS

| 2,945,792 | A | * | 7/1960 | Miller | 522/67 |
|---|---|---|---|---|---|
| 3,989,611 | A | * | 11/1976 | Shurpik | 522/67 |
| 4,094,757 | A | * | 6/1978 | Zapp et al. | 522/27 |
| 4,102,761 | A | * | 7/1978 | Bohm et al. | 522/112 |
| 4,144,154 | A | * | 3/1979 | Zapp et al. | 522/27 |
| 4,162,354 | A | * | 7/1979 | Pearson et al. | 524/305 |
| 4,300,988 | A | * | 11/1981 | Berejka et al. | 525/232 |
| 4,316,941 | A | * | 2/1982 | Eguchi et al. | 428/421 |
| 4,343,864 | A | * | 8/1982 | Berejka | 428/500 |
| 4,682,703 | A | * | 7/1987 | Kasai et al. | 215/247 |
| 4,735,832 | A |   | 4/1988 | Ichikawa et al. | |
| 4,839,429 | A | * | 6/1989 | Tajima | 525/232 |
| 5,082,875 | A | * | 1/1992 | Tajima | 523/103 |
| 5,163,919 | A | * | 11/1992 | Thijs et al. | 604/199 |
| 5,206,043 | A | * | 4/1993 | White | 426/106 |
| 5,228,560 | A | * | 7/1993 | Naslund | 200/275 |
| 5,310,811 | A | * | 5/1994 | Cottman et al. | 525/305 |
| 5,994,465 | A | * | 11/1999 | Sudo et al. | 525/105 |

FOREIGN PATENT DOCUMENTS

| EP | 0 879 611 |   | 11/1998 |
| JP | 60229931 | * | 11/1985 |
| JP | 62070436 | * | 3/1987 |
| JP | 09118346 | * | 5/1997 |

* cited by examiner

Primary Examiner—James J. Seidleck
Assistant Examiner—Sanza L. McClendon
(74) Attorney, Agent, or Firm—Wenderoth, Lind & Ponack, L.L.P.

(57) ABSTRACT

The object of the invention is to provide a rubber composition or its crosslinked product used for a rubber stopper for a medicament or a rubber article for a medical treatment, suitable for radiation treatments to be carried out for the purpose of sterilizing.

Accordingly, the present invention provides a rubber composition or its crosslinked product used for a rubber stopper for a medicament or a rubber article for a medical treatment, comprising an isobutylene copolymer, as a predominant component, with a density of at most 0.95, capable of being readily subjected to a radiation treatment.

2 Claims, No Drawings

RUBBER COMPOSITION USED FOR A RUBBER STOPPER FOR A MEDICAMENT OR FOR A MEDICAL TREATMENT OR ITS CROSSLINKED PRODUCT

BACKGROUND OF THE INVENTION

1. Field of the Invention

This invention relates to a rubber composition for a medical treatment or a medicament, and a crosslinked product thereof, more specifically, a rubber composition used for an instrument for a medical treatment or medicament, or for a rubber stopper for a medicament or a rubber article for a medical treatment, in particular, comprising, as a predominant component, isobutylene copolymers capable of being readily subjected to a radiation treatment.

2. Description of the Prior Art

Use of rubbers in the fields of instruments or containers for medical treatments and medicaments has been started as natural rubbers from the olden time and gradually, synthetic rubbers have often been used. At the present time, thermoplastic elastomers or mixtures with synthetic resins have widely been used. As a test method of such a rubber composition article of this kind (which will hereinafter be referred to as "rubber article"), there are "48 Test Method of Rubber Stopper for Fluid Administration" and "49 Test Method of Plastic Container for Fluid Administration" according to Japanese Pharmacopoeia of 13th Revision, which will hereinafter be referred to as JP 13, in which the passing values are provided. Furthermore, in the field of rapidly advancing articles for medical treatments and for medicaments, it is the present situation that high quality materials and products have been required.

Since about 1950, isobutylene-isoprene copolymer rubbers (which will hereinafter be referred to as "IIR" sometimes), etc. have been recommended as a material suitable for sanitary rubber articles, but cross-linking of IIR is so difficult that a combination of a strong cross-linking agent and cross-linking aid is required. Such a combination is for example described in R. T. Vanderbilt, "RUBBER HANDBOOK", "Vanderbilt" (published 1968), "Gosei Gomu Kako Gijutsu Zensho (Synthetic Rubber Working Technique Complete Book)", Vol. 8, "Butyl Rubber", Taiseisha, (published 1973), etc.

As to the cross-linking technique, there have been proposed a process for the production of adhesives by vulcanization of IIR at a low temperature (JP-A-60-130665), a method for cross-linking IIR in the coexistence of three materials of quinoid, organo peroxides and acryloyl monomer (JP-A-62-074934), cross-linking of IIR in the presence of organo peroxides and polyfunctional monomers having electron-withdrawing groups (JP-A-6-172547), etc.

As a rubber article in the field of requiring high sanitary property are known a rubber article comprising IIR compounded with a fine powder of ultrahigh molecular weight polyethylene (JP-A-60-144346), cross-linking of IIR by joint use of special organo peroxides and maleimides (JP-A-4-213347), etc.

On the other hand, it is apparent that use of butyl rubber most excellent in cleanness as well as gaseous permeability resistance is most suitable as a material of a rubber stopper for medicaments, needing a high sealing degree, for the rubber formulation.

As a method for the sterilization of containers for injections (according to Japanese Pharmacopoeia, a rubber stopper is also defined as a container) and for the sterilization of instruments for medical treatments, the ISO Guide Line or Japanese Pharmacopoeia describes that among a high pressure steam sterilization, gaseous sterilization with ethylene oxide and radiation sterilization, a high pressure steam sterilization is exclusively used for rubber stoppers for medicaments and gaseous sterilization and radiation sterilization are carried out for plastic instruments for medical treatments.

However, the gaseous sterilization method has been considered as a question as to the safety of residual gases in containers or instruments by FDA, etc. and in addition, items for controlling the sterilization step are considered difficult, because of difficulty in controlling or validating a gas concentration or gas temperature distribution, thus making hard identification of the sterilization integrity. Sterilization of a glass container for an injection, rubber stopper thereof or heat resistance plastic instrument for a medical treatment has ordinarily been carried out by a high pressure steam sterilization (autoclave sterilization) from the olden time, which has met a problem with respect to uniform controlling of the temperature in the autoclave and thus, has been subjected to improvement of the system.

For the production of a sterilized container for an injection agent or sterilized instrument for a medical treatment, a sterile test of a final product is an obligation and without passing this test, shipping of the product is impossible, which constitutes a large neck for improvement of the productivity in a production process for instruments for medical treatments. The sterile test requires two weeks until the test results are attained, during which a further step of charging a medicament as a subsequent process cannot be carried out, for example, in the case of a container for the sterile formulation.

FDA in USA has lately proposed the conception that it is equal to adaptability results in the sterile test to control the Parametric Release (shipping being dependent on the parameter administration), that is, the important Parameter for determining the precision of the process and to confirm and record the administrated state. Accordingly, as a first example, there is a sterilization operation utilizing a radiation and in the case of a product sterilized by this method, use and shipping of the product can be allowed by measurement and recording of the absorbed doses of materials sterilized such as containers for injections or instruments for medical treatments before the results of the sterile test. This conception is generally referred to as "Dosimetric Release" (shipping is allowed by dose measurement).

Various synthetic rubbers as raw materials are largely different in radiation resistance depending on their chemical structures, presence or absence of double bond or vinylidene type structure, cross-linking methods, presence or absence of quaternary carbon. EPM and EPDM (ethylene-propylene rubbers and ethylene-propylene terpolymer) having no double bond in the main chain have some problem on the vulcanization property as to working of the rubber, but are used as a material for rubber articles for medical treatments as disclosed by the present inventors in JP-A-62-176455.

On the other hand, the chemical structure of butyl rubber most suitable as a material of a rubber stopper for a medicament consists in having quaternary carbon in the main chain, isobutylene part, so that when applying a high energy such as radiation to the rubber molecule, polymer radicals are produced and the isobutylene part is cut off, resulting in oxidation deterioration. This chemical phenomenon is harder to occur in the case of chemically modified butyl rubber, such as by chlorine or bromine, but the tendency is not changed that it is inferior to any synthetic rubbers in radiation resistance.

The sterilization assurance level (SAL) of a rubber stopper for a medicament or an instrument for a medical treatment is ordinarily provided at $10^{-6}$ and the radiation dose is often used at 25 kGy.

As a radiation, there are α-rays (atomic nucleus of helium), β-rays (electron beam) and γ-rays, and for the sterilization, there are used β-rays prepared by an accelerator and γ-rays generated from $^{60}$Co or $^{137}$Cs. The electron beam has such a higher dose (several $10^4$ times of γ-rays) that the sterilization operation time is short, but only gives a small transmission because of being a particle beam. On the other hand, the γ-rays (X-rays being the same) is a kind of electromagnetic waves and exhibits a large transmission capacity, but takes a longer operation time because of having a smaller dose than the electron beam.

In the case of sterilizing a rubber article by the large transmission γ-rays, the radiation sterilization can be effected even if it is in the form of an article with a large apparent volume wrapped by a corrugated cardboard, but the γ-rays having a smaller dose takes a longer operation time extending to several hours for irradiating a predetermined dose. Such a long irradiation time means a long total irradiation time for an article to be irradiated (article to be sterilized), i.e. a rubber stopper for a medicament, thus resulting in exposure of polymer radicals or peroxyradicals in the rubber, that is, rubber itself to irradiation for a long time leading to oxidation deterioration thereof.

In the rubber technique, it is an antinomic proposition to increase a irradiation dose so as to raise the sterilization assurance level and to suppress deterioration of the rubber material, which is an important problem to be solved in carrying out the radiation sterilization.

SUMMARY OF THE INVENTION

It is an object of the present invention to provide a rubber composition or its crosslinked product used for a rubber stopper for a medicament or a rubber article for a medical treatment, suitable for radiation treatments, whereby the above described problems can be resolved.

It is another object of the present invention to provide a method for the treatment comprising applying a radiation to a rubber composition comprising an isobutylene copolymer, as a predominant component, with a density of at most 0.95 and thereby carrying out crosslinking of said composition or sterilization of the crosslinked product thereof.

These objects can be attained by the following inventions:

(1) a rubber composition or its crosslinked product used for a rubber stopper for a medicament or a rubber article for a medical treatment, comprising an isobutylene copolymer, as a predominant component, with a density of at most 0.95, capable of being readily subjected to a radiation treatment, (2) the rubber composition or its crosslinked product, as described in the foregoing (1), wherein the isobutylene copolymer, as a predominant component, is at least one member selected from the group consisting of isobutylene-isoprene copolymers (IIR), chlorinated isobutylene-isoprene copolymers (C-IIR), brominated isobutylene-isoprene copolymers (B-IIR), crosslinked isobutylene-isoprene-divinylbenzene ternary copolymers (XL-IIR) and brominated isobutylene-paramethylstyrene copolymers (BIMS) and (3) a method for the treatment comprising applying a radiation to a rubber composition comprising an isobutylene copolymer, as a predominant component, with a density of at most 0.95 and thereby carrying out crosslinking of said composition or sterilization of the crosslinked product thereof.

DETAILED DESCRIPTION OF THE INVENTION

In the above described invention (1), the isobutylene copolymer means a copolymer comprising 95 to 99.5 weight % of isobutylene group and 0.5 to 5 weight % of isoprene group, which is ordinarily called IIR. U.S. Pat. Nos. 2,356,128 and 3,816,371 have proposed IIR whose isoprene group content is increased to 30 weight % and such copolymers have commercially been available for some period but have lately disappeared from the market since the prices and uses of the copolymers have not been accepted thereby.

Thus, the object of the present invention is concerned with a generally marketed one as IIR. IIR is an excellent rubber having the feature largely dependent on its isobutylene group and consisting in the chemical stability such as represented by an unsaturated degree of 0, very low gas permeability, high resistance to strong acids such as concentrated sulfuric acid, concentrated hydrochloric acid, etc., to strong alkalies such as concentrated NaOH, etc., to peroxides such as $H_2O_2$, etc., and having a heat resistance as well as a strong stickiness.

In the isobutylene copolymer of the present invention, the isobutylene group is represented by a recurring unit shown by the following formula (1):

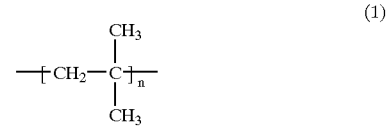

(1)

In this general formula, n is a number of 500 to 150,000.

Since crosslinking of IIR is very difficult, it is known so as to be readily crosslinked to convert it into chlorinated isobutylene-isoprene copolymers (C-IIR) or brominated isobutylene-isoprene copolymers (B-IIR), brominated isobutylene-paramethylstyrene coploymers (BINS) by dissolving IIR in a solvent and then passing through it chlorine gas or bromine gas, and isobutylene-isoprene-divinylbenzene ternary coploymers (XL-IIR) by partially crosslinking IIR with divinylbenzene.

Accordingly, the isobutylene-isoprene copolymerized rubbers of the present invention are exemplified by IIR, BIIR, CIIR and XL-IIR, as described above, which will hereinafter generally be referred to as "IIR member".

As the isobutylene copolymers, there can be used isobutylene-isoprene copolymers (IIR), their chlorinated ones (C-IIR) or brominated ones (B-IIR) or brominated isobutylene-paramethylstyrene coploymers (BIMS), but above all, it is most preferable to use isobutylene-isoprene-divinylbenzene ternary coploymers (XL-IIR) excellent in radiation resistance.

In the present invention, the above described isobutylene copolymers are used as a predominant component, but ordinarily, there can be added thereto thermoplastic resins (plastics or thermoplastic rubbers, TPR) such as high density polyethylene ultrahigh molecular weight polyethylene, methylpentene polymers (TPX), polybutene-1, styreneethylene-butylene-styrene block copolymers (SEBS), ethylene-propylene copolymers (EPM), cyclic olefin homopolymers (COP), cyclic olefin-ethylene copolymers (COC), etc. in a proportion of 10 to 50 weight %.

In the present invention, it is a particularly preferred embodiment that the above described isobutylene copolymers is in a proportion of 70 to 80 weight % to the rubber composition for a medical treatment or medicament.

Furthermore, it is another particularly preferred embodiment that an inorganic reinforcing agent and/or filler in a proportion of 3 to 7 weight parts to 100 weight parts of the above described butyl rubber or isobutylene copolymers and no heavy metal compound is added.

The present invention further provides a rubber article for a medical treatment or a medicament comprising the above described rubber composition crosslinked. This crosslinking is preferably carried out at least one time statically or dynamically using at least one crosslinking means selected from natural crosslinking, heating, using light and irradiating.

The above described crosslinking is generally carried out using a suitable crosslinking agent. As the crosslinking agent, there are ordinarily used, for example, 1,1-di(t-butylperoxy)-3,3,5-trimethylcyclohexane, t-butylcumylperoxide, di-cumylperoxide, 2,5-dimethyl-2,5-di(t-butylperoxy)hexane or -hexin-3, t-butyl-peroxyisopropylcarbonate, benzoylperoxide, di-t-butylperoxide, 2,2'-di-t-butyl-peroxybutane, di-isobutylperoxide, 3-benzoylperoxy-3-methylbutyltriethysilane, pertrimellitic acid tri-t-butyl ester, 3,3',4,4'-tetra(t-butylperoxycarbonyl)-benzophenone, di-t-butylperoxide, t-butylperoxybenzoate, 2,5-di(t-butylperoxy)-2,5-dimethylhexane and the like.

In the rubber composition of the present invention, the isobutylene copolymer is in a proportion of 70 to 80 weight %, since if less than 70 weight %, the features of the copolymers, that is, the gas non-permeability, heat resistance, highly viscous property and chemical stability of polyisobutylene are decreased, while if more than 80 weight %, the deformation and compressive strain of the product are increased. Thus, the product is not preferred as a material for a medical treatment or medicament.

The proportion of the crosslinking compound in the rubber composition according to the present invention is 0.5 to 5 weight parts to 100 weight parts of the IIR member or isobutylene copolymers, since if less than 0.5 weight part, the quantity of strains such as compressive strain is increased to be unsuitable for the use of the present invention, while if more than 5 weight parts, the amounts of expensive additives are increased and not suitable in economy.

To the rubber composition of the present invention can be added at least one member selected from the group consisting of inorganic reinforcing agents or fillers, organic reinforcing agents or fillers, antioxidants, stabilizers and the like in a proportion of 0.5 to 50 weight parts to 100 weight parts of IIR or isobutylene copolymers.

As the inorganic reinforcing agent, for example, silica type fillers, clays, titanium oxide, etc. can be used which are capable of improving thermal and electric conductivity during crosslinking of rubbers, resulting in uniform crosslinking and prevention of the product from deformation. The amount of the inorganic reinforcing agent to be added is preferably in a proportion of 3 to 7 weight parts to 100 weight parts of IIR or isobutylene copolymers, since if more than 7 weight parts, fine grains are caused to be released from the rubber product surfaces, while if less than 3 weight parts, the above described effects cannot be given.

In the present invention, heavy metal compounds having a specific gravity of at least 6.0, such as of lead, cadmium, platinum, etc. are not compounded. It is known that lead compounds such as lead peroxide and lead oxide, etc., chloroplatinic acid, colloidal platinum, tin chlorides, etc. function as a crosslinking aid to shorten the crosslinking time or to improve the crosslinking density of IIR member or isobutylene copolymers, but in the present invention, these compounds are not used even if the crosslinking effect is present, since the presence of heavy metals should be avoided in the application field as a final rubber article. Because of using no such compounds, the rubber composition of the present invention is capable of giving high sanitary property and passing the standards of various official propvisions.

To the rubber composition of the present invention can further be added organic type reinforcing agents, antioxidants, stabilizers, etc. As the particularly preferred organic type reinforcing agents, there are ultrahigh molecular weight polyethylene powder (e.g. Hizexmillionmeter 240, commercial name), polyethylene (PE), polypropylene (PP), polycarbonate (PC), polybutadiene (BR), 1,2-bonded styrene butadiene (SBR), polysulfone type resins (e.g. VDEL, commercial name) and the like, at least one of which can be used in a proportion of 20 to 30 weight parts to 100 weight parts of the IIR member or isobutylene copolymers.

As the crosslinking assistant, there can be used silane coupling agents such as vinyltrimethoxysilane, γ-methacryloxypropyltrimethoxysilane, γ-glycidoxypropyltrimethoxysilane, γ-mercaptopropyltrimethoxysilane, β-(3,4-epoxycyclohexyl)ethyltrimethoxysilane, etc., tetrakis(2-ethylhexyl) titanate, dipropoxy-bis(acetylacetonato)titan [titanacetylacetonato], sulfur, stearic acid, triallyl cyanurate, triallyl isocyanurate, trimethylolpropane trimethacrylate, 1,2-polybutadiene, m-phenylenebismaleimide, magnesium oxide, titanium oxide, zinc oxide, bis(2-diethylamino)-4,6-dimercapto-s-triazine and the like, at least one of which can be added in a proportion of 0 to 5 weight parts to 100 weight parts of IIR member or isobutylene copolymers.

Furthermore, as the antioxidant, for example, there can be used 2,6-di-t-butyl-p-cresol, n-octadecyl-β-(4'-hydroxy-3', 5'-di-t-butylphenyl)propionate, tetrakis[methylene-3(3',5'-d-t-butyl-4-hydroxyphenyl)propionate]methane and the like, at least one of which can be added in a proportion of 0.05 to 1 weight part to 100 weight parts of IIR member or isobutylene copolymers.

The variety and quantity of compounding agents are varied with a number of factors, for example, instruments for medical treatments, kinds of instruments for medicaments, required properties, effects, machines or tools for shaping or working, producibility, unit costs, etc. Since shaping and crosslinking of the IIR member are one of the largest difficulties, it is important to prepare rubber articles having the most suitable properties for medical treatments and medicaments by combining many factors for designing products.

In the present invention, the crosslinking is carried out by either a static method comprising crosslinking and shaping using a metallic mold or a dynamic method shaping after dynamic crosslinking using an extruder, internal mixer, curl, etc.

As the crosslinking means, there can be used heating, light irradiation or application of radiation. In the case of the thermal crosslinking, there are a method comprising heating at a temperature of 140 to 200° C. in a metallic mold and thus effecting crosslinking and shaping or a method comprising heating at a temperature of 140 to 300° C. in an internal mixer or extruder, thus effecting dynamic crosslinking and then shaping.

The crosslinking by radiation can preferably be carried out by application of an absorbed dose of 50 kGy to 200 kGy, in particular, electron beam. In a special case, a crosslinking agent is added in a proportion of at least 0.5 weight part to 100 weight parts of a composition, as an ordinary embodiment, corresponding to a minimum quantity required for the static crosslinking or dynamic crosslinking, and the thus shaped article is taken out of a metallic mold, subjected to punching into a sheet and then to application of an electron beam with an absorbed dose of 50 kGy to 200 kGy again.

The rubber article of the present invention, obtained by crosslinking and shaping, is then rinsed and if necessary, subjected to a known treatment as an article for a medical treatment or an article for a medicament, for example, to a sterilization treatment. Practical crosslinking and aftertreatment conditions will concretely be illustrated by the following examples.

In the above described invention (3), application of a radiation to the rubber composition is carried out for the purpose of crosslinking the composition or sterilizing the crosslinked product thereof, and the radiation resistance thereof is dependent on the physical properties, chemical structures, presence or absence of double bonds or vinylidene type structures, crosslinking methods, presence or absence of quaternary carbons, of the composing resin components.

In the present invention, the radiation used includes α-rays (atomic nucleus of helium), β-rays (electron beam) and γ-rays. For the sterilization, β-rays (electron beam) made by an accelerator, γ-rays generated from $^{60}$Co or $^{107}$Cs are preferable. Since the electron beam has a very high dose (as large as several $10^4$ times γ-rays), the sterilizing treatment time can be shortened, but its transmission capacity is smaller because of being a corpuscular beam. On the other hand, the γ-rays (x-rays is the same) is a kind of electromagnetic waves and exhibits a large transmission capacity, but takes a longer operation time because of having a smaller dose than the electron beam.

In the case of sterilizing a rubber article by the large transmission γ-rays, the radiation sterilization can readily be effected even if it is in the form of an article with a large apparent volume wrapped by a corrugated cardboard, but the γ-rays having a smaller dose takes a longer operation time extending to several hours for irradiating a predetermined dose.

As illustrated before, when radiation is applied to sterilize a vulcanized rubber (rubber article), the exposure dose (absorption dose) is the larger, the rubber article is the more largely affected. In the case of butyl rubber (IIR member), in particular, this tendency is present, so the lower limit of the exposure dose should necessarily be provided with a higher level when an article to be sterilized has a higher degree of microorganism contamination (larger number of adhered bacteria).

In ISO 11171-1997, it is provided that when medical devices or health care products are subjected to radiation sterilization, the total number of adhered bacteria per one product must be at most 100. Assuming that Do value of *Bacillus Pumilus* is 1.7 kGy and all the adhered bacteria are present on the inner surface of a container, the theoretical number of surviving bacteria, as can be expected, is $99 \times 10^{-2}>$ with a dose of 3.4 kGy and $99 \times 10^{-6}>$ with a dose of 10.2 kGy.

At the present time, radiation sterilization of plastic medical devices such as syringes of polypropylene and artificial analyzer of polycarbonate has generally been carried out by applying 25 kGy, while in the present invention, the application of radiation for the purpose of sterilizing rubber stoppers for medicaments or rubber articles for medical treatments is generally carried out using a radiation dose of 5 kGy to 30 kGy in suitable manner.

Since the γ-rays is capable of exhibiting a higher transmission capacity (smaller attenuation coefficient), there is no large difference between the absorbed doses of an incident surface and back surface or adjacent reincident surfaces. That is, the method using γ-rays is a preferred means as a method of uniformly sterilizing a number of articles to be irradiated in the form of a singly wrapped state. Application of electron beam having a large dose results in marked reduction of an amount of a crosslinking agent in the prior art and thus, can be used as a method of crosslinking raw rubber (utilizing formation of polymer free radicals). Accordingly, this is a means capable of obtaining a finally aimed quality and property level of a rubber article for a medicament or medical treatment by subjecting a previously molded TPE (TPR) to secondary crosslinking (or post-crosslinking) or as in Examples 4 to 6 (Table 1), by subjecting a molding obtained by crosslinking a previously molded and pressed product (heating in a primary shaping stage) and adding a very small amount of crosslinking agent required for molding an original form to application of electron beam (secondary crosslinking).

The inventors have made various efforts and consequently, have found that when a rubber stopper for a medicament comprising butyl rubber excellent in sealing property is sterilized by application of radiation, with the proviso, as a primary optimum sterilizing condition, that electron beam is selected as a beam source and the degree of microorganism contamination on the surface of an article to be sterilized is low, use of a rubber stopper which is designed to decrease its density, in particular, to at most 0.95, so that electron beam is sufficiently transmitted by the application of a dose as low as possible for sterilizing and in a short period of time, is effective for readily transmitting radiation and advancing the radiation treatment with less oxidation and deterioration of the resin. The present invention is based on this finding.

In this case, the oxidation and deterioration of the resin is caused by such a phenomenon that polymer radicals are reacted with oxygen dissolved or diffused from the outside to form peroxy radicals (—O* *O—) and the quarternary carbon part is cut to give R—C=O and the molecular principal chains are cut to reduce the molecular weight (i.e. phenomenon occurring with passage of time) and that the principal chains are directly cut by radiations such as γ-rays, electron beam, etc. (i.e. phenomenon occurring directly after irradiation).

For the purpose of decreasing the density of the rubber composition of the present invention or its crosslinked product to at most 0.95, the blending proportion of components is controlled depending on the relationship of densities of IIR member, that is, IIR<C-IIR and B-IIR<XL-IIR or the blending proportion of additive components to be added such as thermoplastic resins, organic auxiliary agents, fillers, etc. is controlled, thus obtaining the relationship of $d \leq 0.95$.

EXAMPLES

The following Examples are given in order to illustrate the invention in detail without limting the same.

Treatment methods and measurement methods shown in Examples will now be illustrated.

Procedure of Irradiation Experiment (Preparation of Sample)

Using compositions (non-crosslinked or non-vulcanized) compounded according to rubber formulations described in Examples 1 to 5 and Comparative Examples 1 to 6, rubber sheets each having a thickness of 10 mm and a length×width of 100 mm×100 mm are subjected to crosslinking (or vulcanizing) and shaping to obtain a Sample a.

Sample a is cut in 10 mm long and 10 mm broad and subjected to a washing treatment so as to pass the official standard for a rubber stopper, "Test Method of Rubber Stopper for Fluid Administration" or "Elution Test" according to Japanese Pharmacopoeia of 13th Revision to obtain a Sample b.

Similarly, a rubber stopper with a flange diameter of 20 mm, leg diameter of 13 mm and flange thickness of 3 mm is shaped and subjected to a predetermined washing treatment to obtain a Sample c (rubber stopper type).

Sample a is used for measurement of the transmitted dose of electron beam or γ-rays (reaching the back surface of the irradiated surface), Sample b for the chemical test of the official standard (Japanese Pharmacopoeia) and Sample c for the physical test (functional property test).

Irradiation Conditions of Radiations (γ-Rays and Electron Beam)

Irradiation Conditions of γ-Rays

Sample a (plate-like) or Sample c (rubber stopper-like in polyethylene bag) is fitted to a support plate (corrugated cardboard of 40 mm thick) vertically fixed in a push car of box type for irradiation of γ-rays. A measurement dosimeter (Harwell Red Perspex Dosimeter Type 4034 Batch FC) is pasted to a part of the irradiated surface of the sample or its back surface and then the push car of box type for irradiation is passed through the front of the beam source $^{60}Co$ to irradiate the sample by an expected surface dose of 25 kGy of γ-rays.

Irradiation Conditions of Electron Beam

[Sample Treatment (Preparation)]

Samples a, b and c are mounted on a cart support material (corrugated cardboard of 40 mm thick) of a cart push car for irradiation (cart of SUS of 1,500 mm×950 mm). CAT dosimeter FTR-125 (commercial name, manufactured by Fuji Photo Film Co., Ltd.) is arranged on a part of the irradiated surface of the sample or its back surface and an expected surface dose of 25 kGy of electron beam is irradiated using 5 MeV Dinamitron type Electron Accelerator (commercial name, manufactured by RDI (USA)), which each of irradiation perameters is determined in an acceleration voltage of 5.0 MV, current of 25 mA and cart outer circumferential velocity of 15 m/min.

Measurement of Surface Absorption Dose (Irradiation Dose) and Transmission Dose

Using a Dosimeter U-2000 Spectro Photometer (commercial name, manufactured by Hitachi Seisakujo Co., Ltd.), measurement of the absorbance is carried out as to all the dosimeters used in the tests for the irradiation of γ-rays and electron beam, and the absorption dose is calculated based on the calibration curve previously prepared.

Measurement of Crosslinking Density

A rubber sample piece of 1 mm thick×2 mm broad×10 mm long is cut out of the rubber sample piece of 10 mm thick, charged in a test tube with cyclohexane having a volume of about 10 to 20 times as large as the rubber sample piece in such a manner that the rubber sample piece is suspended by a silk yarn and immersed therein, but is not brought into contact with the inner wall of the test tube and is tightly sealed.

While the whole of the test tube is maintained at 20 to 30° C., the rubber sample piece is taken out of the test tube sometimes at an interval of about 8 hours, immediately subjected to wiping-off of the surface by a filter paper and then charged in a weighing vial to precisely weigh the weight thereof, followed by recording. When increase of the weight of the rubber sample piece reaching equilibrium swelling is stopped after repetition of this procedure, the immersion in the solvent is finished. From the weight of the rubber sample piece reaching the equilibrium swelling, the crosslinking density is calculated using the following Flory-Rehner's Formula 1). The crosslinking density is defined herein by the number of crosslinked points present in unit volume.

$$v = \frac{1}{V}\left(\frac{\ln(1-V_R) + \mu V_R^2}{V_R^{1/3} - 2V_R/f}\right) \qquad 1)$$

v: network chain density (mol/cm$^3$)

f: functionality (defined as 4) of crosslinking $V_R$: volume fraction of rubber in swelled gel (volume of rubber gel of sample before swelling/volume of rubber gel swelled)

V: molecular volume (cm$^3$/mol) of solvent (cyclohexane)

μ: solvent-rubber interaction coefficient

Measurement of Density of Vulcanized Product (Procedure of Test)

Each Sample a prepared according to corresponding conditions is cut in a size of about 10 mm long, about 1 mm broad and about 1 mm thick. A piece of the cut Sample a is combined by passing through a very fine silk yarn positioned as near the end part as possible and cut to retain a suitable length of about 15 cm. A piece of the silk yarn fitted Sample a is charged in a weighing vial of No. 9 (self weight about 8 g) and sealed by a ground glass stopper. Then, the whole weight is precisely measured to a unit of mg using a chemical balance of digital type.

The Sample a is suspended in a glass-made Nessler's tube of 30 mL (manufactured by Pyrex length of 200 mm, outer diameter of 21 mm), in which 20 mL of cyclohexane has been charged, under sealed state by the use of a separately prepared rubber stopper without using any ground glass stopper. During the same time, it is to be noted that Sample a (rubber small piece) is not contacted with the inner wall or bottom part of the glass tube. The Nessler's tube is inserted in a test tube stand and allowed to stand at room temperature, 20 to 25° C. until Sample a reaches equilibrium swelling (ordinarily, 3 to 5 days depending on the rubber formulation or crosslinking density).

When Sample a reaches the equilibrium swelling, the silk yarn-attached Sample a is taken out of the Nessler's tube, immediately wiped off by a lint-free cloth to remove the cyclohexane adhered to the sample part, charged in the weighing vial and tightly sealed to measure precisely the whole weight.

(Calculation of Crosslinking Density)

Each of the measured values is substituted for the following fundamental formula 2) of Flory-Rehner to calculate the crosslinking density of each Sample a:

$$v = gv' = -\frac{g}{V}\left(\frac{\ln(1-V_R) + V_R \mu V_R^2}{g^{2/3}V_R^{1/3} - V_R/2}\right) \quad 2)$$

$$v = -\frac{1}{V}\left(\frac{\ln(1-V_R) + V_R + \mu V_R^2}{V_R^{1/3} - 2V_R/f}\right) \quad 3)$$

v: network chain density (mol/cm$^3$) of gelled rubber in swelled test piece (Sample a piece)

V: molecular volume of swelled solvent (cyclohexane), i.e. molecular weight/density (cm$^3$/mol)

g: volume fraction of gelled rubber in test piece (Sample a piece) before swelling $\mu$: interaction constant of test piece (Sample a piece) and swelled solvent (cyclohexane), citing 0.55 (cyclohexane) as $\mu$ value of PIB in Bawn et al: Trans. Faraday Soc. 52 (1956), 1664 and Bayer's measured $\mu$ value, i.e. 0.6 (cyclohexane) as to three-dimensionally crosslinked butyl rubber $V_R$: molecular fraction of rubber in swelled rubber f: 4

Measurement of Transmission Dose (Dose Reaching Back Surface)

A higher density rubber composition (crosslinked product) encounters such a phenomenon that applied radiation or electron beam tends to attenuate so that there occurs a large difference in absorption dose between the incident surface and the inner part or back surface of the body to be irradiated such as rubber stoppers for medicaments, rubber instruments for medical treatments, rubber parts for medical treatment instruments, etc., and the surface vicinity of the body to be irradiated is strongly deteriorated. An attenuated portion can be supplemented by the increased irradiation dose, but if so, the difference in absorption dose between the incident surface and the inner part or back surface of the body to be irradiated, as described above, is more and more increased, resulting in a larger problem. In order to clarify the relationship between the density of the specified rubber composition (crosslinked rubber product) according to the present invention and the irradiation dose and transmission dose (=irradiation dose−absorption dose, attenuation part), it is a desired condition to ordinarily adjust the irradiation dose (substituted by the absorption dose) to at least 25 kGy sufficient to realize a sterilization guarantee level of 10$^{-6}$ for an instrument for a medical treatment.

Measurement of Change (pH change) of Liquid Property of WFI

Measurement of Change of Liquid Property of Injection Water (WFI)

(Preparation of Sample)

10 mL of water for injection (WFI, commercially available) is charged in a glass vial (commercially available) with a volume of 10 mL, whose inside is cleaned, stoppered by a Sample c (rubber stopper for medicament), covered by an aluminum cap (commercially available, which can be made of plastic), fastened by a hand clipper and tightly sealed. WFI obtained by storage under inverted state at an accelerated condition of 40° C. for at least 6 months is used as a test liquid.

(Measurement of pH)

The test liquid (WFI) prepared by the foregoing procedure is subjected to measurement of pH according to "Test Method of Rubber Stopper for Fluid Administration" or "Elution Test" according to Japanese Pharmacopoeia of 13th Revision.

Measurement of Liquid Leakage 10 mL of water is charged in a glass vial (commercially available) with a prescribed volume of 10 mL, stoppered by a Sample c (rubber stopper for medicament), covered by an aluminum cap (commercially available, which can be made of plastic), fastened by a hand clipper and tightly sealed. An upper cover of the aluminum cap, which can be made of plastic, is removed, while an injection needle of 18 G is fitted to a disposable syringe to suck 2 mL of air and then vertically pierced through the Sample c to feed 2 mL of the foregoing air into the vial. After feeding the air, the vial is rapidly inverted, 2 mL of the water is sucked, the injection needle is slowly withdrawn and then the weight of the liquid leaked is measured.

As a general allowance value, the total leaked quantity is at most 0.1 mL (0.1 g).

Coring Test 10 mL of water is charged in a vial (commercially available) with a prescribed volume of 10 mL, stoppered by a Sample c (rubber stopper for medicament), covered by an aluminum cap (commercially available, which can be made of plastic), fastened by a hand clipper and tightly sealed. An upper cover of the aluminum cap, which can be made of plastic, is removed, while after sucking 2 mL of water in the disposable syringe, an injection needle of 18 G is fitted thereto, and vertically pierced through the Sample c (rubber stopper for medicament) at random four times. Then, the water in the syringe is injected into the vial and the injection needle is withdrawn.

The vial is shaken several time vertically and the number of released pieces of the Sample c (rubber stopper for medicament) is counted.

During the same time, the surface state of the Sample c (rubber stopper for medicament) is visually observed by means of a microscope and presence or absence of the traces of releasing is confirmed. As a general allowance value, the number of released pieces of the Sample c for piercing 40 times at random should be at most two.

Chemical Adaptation Test of Rubber Stopper (Preparation of Test Liquid)

In a clean beaker with a volume of 300 mL is taken a Sample b (weight of one sample: 0.93 to 1.3 g), as a test body, with a total weight of at least 20 g (16 to 22 samples), after which distilled water with a volume of as large as ten times the weight of their samples is added. The upper part of the beaker is loosely covered by a suitable cover, placed in an autoclave and heated at 121° C. for 60 minutes. The Sample b is immediately taken out of the autoclave and allowed to stand at room temperature, after which the elution of the Sample b is subjected to decantation and used as a test liquid.

(Test Method)

The thus prepared test liquid (aqueous elution of Sample b) is subjected to estimation of their liquid properties (consumption amount of potassium permanganate, difference of pH values, absorbance of UV part, transmission percent of visible ray part) according to the official standard for a rubber stopper, "Test Method of Rubber Stopper for Fluid Administration" or "Elution Test" of Japanese Pharmacopoeia of 13th Revision.

Test for Estimation of Functionality of Rubber Stopper

This test is carried out by the following four stage estimation method.

Four Stage Estimation Test:

⊚: much more excellent than standard value

○: passing standard value

Δ: not passing standard value

X: much worse than standard value

Examples 1 to 6 and Comparative Examples 1 to 6

100 parts by weight of C-IIR (manufcatured by Esso Chemical Co., Ltd., Esso Butyl HT 1066, commercial name), 15 parts by weight of high density polyethylene powder (manufactured by Mitsui Kagaku Co., Ltd., Millason 68P, commercial name), 1 part by weight of styrene-ethylene-butylene-styrene thermoplastic rubber (manufacture by Shell Kagaku Co., Ltd., Kraton® G1650, commercial name), 1 part by weight of magnesium oxide (manufactured by Kyowa Kagaku Kogyo Co., Ltd., Kyowa-Mag® 150, commercial name) and 2 parts by weight of s-triazine were blended (Example 1). The blending operation was carried out at a roll temperature of 60 to 90° C. according to SRIS [Nippon Rubber Association Standard 3604 (1980)]. As shown in Table 1, similar blends within the scope of the present invention and outside the scope of the present invention were respectively prepared as Examples 2 to 6 and Comparative Examples 1 to 6 in similar manner.

The results are shown in Table 1.

TABLE 1

|  | Example | | | | | | Comparative Example | | | | | |
| --- | --- | --- | --- | --- | --- | --- | --- | --- | --- | --- | --- | --- |
|  | 1 | 2 | 3 | 4 | 5 | 6 | 1 | 2 | 3 | 4 | 5 | 6 |
| Compounding Agent and Test Conditions | | | | | | | | | | | | |
| C-IIR 1) | 100 | | | 100 | | | 100 | 100 | 80 | 100 | | |
| X-IIR 2) | | 100 | | | 100 | | | | | | 100 | |
| IIR 3) | | | 100 | | | 100 | | | 20 | | | 100 |
| Hydrated Silica 4) | | 6 | 5 | | 6 | 5 | | 15 | | | 15 | 15 |
| Calcined Clay 5) | | | | | | | 25 | 35 | 62 | 25 | 35 | 35 |
| UHMWPE 6) | | 20 | | | 20 | | | | | | | |
| HDPE 7) | 15 | | | 10 | 15 | | 10 | | | | | |
| SEBS 8) | 5 | | | 5 | | | | | | | | |
| Titanium Oxide 9) | | | | | | | 5 | 5 | 10 | 5 | | |
| Carbon Black 10) | | | | | | | 0.5 | 0.5 | 0.5 | 0.5 | | |
| Magnesium Oxide 11) | 1 | | | 1 | | | 1 | 0.2 | 1 | 1 | | |
| Zinc Oxide 12) | | | | | | | | 5 | 5 | | | |
| Stearic Acid 13) | | | | | | | | 0.5 | 1 | | | |
| DPTT 14) | | | | | | | | | | | | |
| ZBDC 15) | | | | | | | | 2 | 2 | | | |
| s-Triazine 16) | 2 | | | 0.5 | | | 2 | | | 0.5 | | |
| m-PBM 17) | | 2 | | | 1 | | | | | | | 1 |
| TAIC 18) | | 2 | | | 0.5 | | | | | | | 0.5 |
| Fine Powder Sulfur 19) | | | | | | | | | | | | |
| Organo Peroxide 20) | | 2 | 1 | | 0.1 | 0.5 | | | | | 0.1 | 0.5 |
| Crosslinking (Vulcanizing) Conditions, Crosslinking Temperature (° C.) × Time (min) | | | | | | | | | | | | |
| Primary Crosslinking | 175 × 10 | 180 × 10 | 170 × 10 | 175 × 10 | 180 × 10 | 170 × 10 | 175 × 10 | 175 × 10 | 175 × 10 | 175 × 10 | 180 × 10 | 170 × 10 |
| Secondary Crosslinking kGy (Electron Beam Irradiation) | | | 100 | 50 | | 200 | | | | 100 | 50 | 200 |
| Property Test | | | | | | | | | | | | |
| Density of Crosslinked Product (g/cm$^3$) | 0.93 | 0.95 | 0.95 | 0.93 | 0.95 | 0.95 | 1.11 | 1.19 | 1.30 | 1.09 | 1.16 | 1.16 |
| Crosslinking Density (×10$^{-5}$ mol/cm$^3$) | 33.1 | 25.5 | 21.7 | 35.3 | 37.0 | 24.7 | 8.29 | 6.65 | 6.9 | 10.5 | 18.2 | 7.07 |
| Test Conditions and Estimation | | | | | | | | | | | | |
| Transmission Dose (kGy) g/cm$^3$ | | | | | | | | | | | | |
| Electron Beam | 29 | 27 | 27 | 26 | 24 | 24 | 14 | 11 | 7 | 13 | 11 | 12 |
| γ-Rays | 25 | 24 | 24 | 24 | 24 | 24 | 23 | 24 | 15 | 24 | 23 | 23 |
| Surface State (Finger Touch Feeling) | non-sticky | non-sticky | non-sticky | non-sticky | non-sticky | non-sticky | little sticky | sticky | sticky | little sticky | sticky | little sticky |
| Liquid Property Change of WFI (pH change) | +0.2 | +0.5 | −0.2 | −0.1 | +0.1 | −0.3 | +1.3 | +1.6 | +1.2 | +0.9 | +0.7 | +0.5 |
| Official Procedure Test (Japanese Pharmacopoeia) | | | | | | | | | | | | |
| Chemical Test | | | | | | | | | | | | |
| Consumption Amount of Potassium Permanganate (ml) | 0.3 | 0.2 | 0.4 | 0.2 | 0.0 | 0.2 | 0.5 | 0.9 | 0.7 | 0.4 | 0.9 | 1.2 |
| pH Value Difference from Blank Value | −0.1 | +0.1 | +0.2 | +0.2 | −0.1 | −0.1 | +0.2 | +0.6 | +1.1 | +0.9 | +0.5 | +0.7 |
| Absorption at UV Part 220 nm / 350 nm (Absorbance) | 0.02 | 0.01 | 0.03 | 0.02 | 0.00 | 0.02 | 0.01 | 0.03 | 0.100 | 0.08 | 0.05 | 0.07 |

TABLE 1-continued

|  | Example | | | | | | Comparative Example | | | | | |
| --- | --- | --- | --- | --- | --- | --- | --- | --- | --- | --- | --- | --- |
|  | 1 | 2 | 3 | 4 | 5 | 6 | 1 | 2 | 3 | 4 | 5 | 6 |
| Percent Transmission | 100.0 | 100.0 | 99.5 | 99.9 | 100.0 | 99.9 | 99.9 | 99.9 | 98.9 | 99.9 | 100.0 | 99.8 |
| 430 nm / 659 nm (%) | 100.0 | 100.0 | 100.0 | 99.9 | 100.0 | 100.0 | 99.9 | 100.0 | 99.9 | 100.0 | 100.0 | 99.9 |
| Physical Test | | | | | | | | | | | | |
| Hardness JIS A Type (degree) | 42 | 40 | 40 | 43 | 43 | 40 | 46 | 44 | 43 | 44 | 40 | 39 |
| Liquid Leakage Test (ml) | 0.0 | 0.0 | 0.0 | 0.0 | 0.0 | 0.0 | 0.8 | 0.5 | 0.3 | 1.5 | 0.4 | 1.0 |
| Coring Test (released pieces / total number of needle piercing) | 0/40 | 0/40 | 0/40 | 0/40 | 0/40 | 0/40 | 5/40 | 8/40 | 12/40 | 4/40 | 3/40 | 10/40 |
| Estimation of Chemical Adaptability of Rubber Stopper | ○ | ○ | ○ | ◎ | ◎ | ◎ | X | X | X | ○ | Δ | X |
| Estimation of Functionality of Rubber Stopper | ◎ | ◎ | ◎ | ◎ | ◎ | ◎ | X | X | X | X | X | X |

[Note]
1) Esso Butyl HT 1066, Chlorinated butyl rubber, commercial name, manufactured by Esso Kagaku Co., Ltd.)
2) Bayer Butyl XL-10000, isoprene-isobutylene-divinylbenzene ternary copolymer crosslinked butyl rubber, commercial name, manufactured by Bayer AG. (Canada)
3) Esso Butyl 365, isoprene-isobutylene copolymer type butyl rubber, commercial name, manufactured by Esso Kagaku Co., Ltd.
4) Nipsil VN-3, wet process silica, commercial name, manufactured by Nippon Silica Kogyo Co., Ltd.
5) White Tex Clay # 2, commercial name, manufactured by Southern Clay (USA)
6) Mipelon ® 220, ultrahigh molecular weight polyethylene resin fine powder, commercial name, manufactured by Mitsui Kagaku Co., Ltd.
7) Mirason ® 68P, high density polyethylene resin pellets, commercial name, manufactured by Mitsui Kagaku Co., Ltd.
8) Kraton ® G1650, styrene-ethylene-butylene-styrene thermoplastic rubber, commercial name, manufactured by Shell Kagaku Co., Ltd. (USA)
9) Tipaque ® A100, titanium dioxide of anatase type, commercial name, manufactured by Ishihara Sangyo Co., Ltd.
10) Therm Black ® MT, medium thermal carbon black, commercial name, manufactured by Cancab Co., Ltd. (Canada)
11) Kyowa-Mag ® 150, active magnesium oxide, commercial name, manufactured by Kyowa Kagaku Kogyo Co., Ltd.
12) JIS Standard, first class zinc oxide, manufactured by Mitsui Kinzoku Kozan Co., Ltd.
13) Lunac S30, stearic acid, commercial name, manufactured by Kao Co., Ltd.
14) Nocceler ® TRA, dipentamethylenethiuram tetrasulfide, commercial name, manufactured by Ouchi Shinko Kagaku Kogyo Co., Ltd.
15) Accel BZ, zinc dibutyldithiocarbamate, commercial name, manufactured by Kawaguchi Kagaku Kogyo Co., Ltd.
16) Zisnet DB, 2-di-n-butylamino-4,6-dimercapto-s-triazine, commercial name, manufactured by Sankyo Kasei Co., Ltd.
17) Sumifine BM, N,N'-m-phenylenebismaleimide, commercial name, manufactured by Sumitomo Kagaku Kogyo Co., Ltd.
18) TAIC, triallyl isocyanurate, commercial name, manufactured by Nihon Kasei Co., Ltd.
19) fine powder sulfur, manufactured by Karuizawa Seirenjo Co., Ltd.
20) Perhexa 2.5 B 100% Product, 2,5-dimethyl-2,5-bis-(t-butylperoxy) hexane, commercial name, manufactured by Nihon Yushi Co., Ltd.

The results of Examples 1 to 6 and Comparative Examples 1 to 6 shown in Table 1 (continued) are estimated as follows. In Examples 1 to 3, various butyl rubbers (raw rubbers) are prepared by the standard procedures in such a manner that the density of the composition (same as density of crosslinked product) be at most 0.95, and in Examples 4 to 6, it is disclosed that the crosslinking agents of Examples 1 to 3 are decreased near the lower limit required for obtaining the primary crosslinked product (or preliminary molding) and electron beam having an absorption dose of 50 kGy to 200 kGy is applied to the thus obtained crosslinked product to obtain a crosslinking density (also referred to as vulcanization degree) of at least the similar crosslinking density thereto. On the contrary, Comparative Examples 1 to 3 and 4 to 6 disclose the cases where the densities of the compositions or crosslinked products exceed 0.95 (in practice, 1.09 to 1.30). As described above, the object of irradiating γ-rays is to sterilize the crosslinked product and electron beam is used for increasing the density of the crosslinked product (correctly, primary crosslinked product or preliminary crosslinked product) to the aimed crosslinking density. From these results, it is apparent that the composition or crosslinked product has a criticallity of a density of at most 0.95.

Examples 7 to 10 and Comparative Examples 7 to 12

The procedure of Example 1 was repeated except changing the compounding components and compounding proportions into as shown in Table 2, thus obtaining results shown in Table 2 (continued). Thus, substantially similar results to Examples 1 to 6 and Comparative Examples 1 to 6 were obtained.

TABLE 2

|  | Example | | | | Comparative Example | | | | | |
| --- | --- | --- | --- | --- | --- | --- | --- | --- | --- | --- |
|  | 7 | 8 | 9 | 10 | 7 | 8 | 9 | 10 | 11 | 12 |
| Compounding Agent and Test Conditions | | | | | | | | | | |
| IIR 3) | 100 | 100 | 100 | 100 | 100 | 80 | 80 | 100 | 80 | 80 |
| C-IIR 1) |  |  |  |  |  | 20 | 20 |  | 20 | 20 |
| Hydrated Silica 4) |  | 5 |  | 5 | 5 |  |  | 5 |  |  |
| Calcined Clay 5) |  |  |  |  |  | 5 | 48 | 62 | 5 | 48 | 62 |

TABLE 2-continued

|  | Example | | | | Comparative Example | | | | | |
|---|---|---|---|---|---|---|---|---|---|---|
|  | 7 | 8 | 9 | 10 | 7 | 8 | 9 | 10 | 11 | 12 |
| UHMWPE 6) | 20 |  | 20 |  |  |  |  |  |  |  |
| HDPE 7) |  |  |  |  |  |  |  |  |  |  |
| Carbon Black 10) |  |  |  |  | 0.5 |  |  | 0.5 |  |  |
| Titanium Oxide 9) |  |  |  |  | 5 | 10 | 10 | 5 | 10 | 10 |
| Zinc Oxide 12) |  |  |  |  |  | 5 | 5 | 1 | 5 | 5 |
| Stearic Acid 13) |  |  |  |  |  | 1 | 1 | 2 |  | 1 |
| DPTT 14) |  |  |  |  |  | 2 | 2 |  |  | 2 |
| m-PBM 17) | 2 | 2 | 2 | 2 | 2 |  |  | 2 |  |  |
| TAIC 18) | 2 | 2 | 2 | 2 | 2 |  |  | 2 |  |  |
| Organo Peroxide 20) | 1 | 1 | 1 | 1 | 1 |  |  | 1 |  |  |
| Crosslinking (Vulcanizing) Conditions, Crosslinking Temperature (° C.) × Time (min) |  |  |  |  |  |  |  |  |  |  |
| Primary Crosslinking | 170 × 10 | 170 × 10 | 170 × 10 | 170 × 10 | 170 × 10 | 175 × 10 | 175 × 10 | 170 × 10 | 175 × 10 | 175 × 10 |
| Secondary Crosslinking kGy (Electron Beam Irradiation) |  |  | 100 | 100 |  |  |  | 100 | 100 | 100 |
| Property Test |  |  |  |  |  |  |  |  |  |  |
| Rubber Fraction in Recipe (vol %) | 82 | 97 | 82 | 97 | 95 | 83 | 80 | 95 | 83 | 80 |
| Density of Crosslinked Product (g/cm$^3$) | 0.93 | 0.95 | 0.93 | 0.95 | 1.01 | 1.25 | 1.30 | 1.01 | 1.25 | 1.30 |
| Crosslinking Density (×10$^{-5}$ mol/cm$^3$) | 25.6 | 20.9 | 27.8 | 24.1 | 9.03 | 6.88 | 4.75 | 8.1 | 7.3 | 5.4 |
| Transmission Dose (kGy) g/cm$^2$ (25 kGy irradiation) |  |  |  |  |  |  |  |  |  |  |
| Electron Beam | 25 | 26 | 28 | 25 | 13 | 8 | 6 | 14 | 9 | 7 |
| γ-Rays | 24 | 25 | 24 | 24 | 22 | 16 | 16 | 23 | 12 | 15 |
| Surface State (Finger Touch Feeling) | non-sticky | non-sticky | non-sticky | non-sticky | little sticky | strong sticky | stronger sticky | strong sticky | strong sticky | stronger sticky |
| Liquid Property Change of WF (pH change) | −0.2 | −0.1 | −0.4 | −0.5 | +0.9 | +1.1 | +0.8 | +0.5 | +0.8 | +0.5 |
| Test Conditions and Estimation |  |  |  |  |  |  |  |  |  |  |
| Official Procedure Test (Japanese Pharmacopoeia) |  |  |  |  |  |  |  |  |  |  |
| Chemical Test |  |  |  |  |  |  |  |  |  |  |
| Consumption Amount of Potassium Permanganate (ml) | 0.5 | 0.3 | 0.6 | 0.7 | 1.0 | 1.3 | 0.8 | 1.3 | 1.5 | 1.1 |
| pH Value Difference from Blank Value | +0.1 | +0.3 | −0.2 | +0.1 | −0.3 | +1.2 | +0.8 | −0.7 | −1.2 | −0.8 |
| Absorption at UV Part 220 nm / 350 nm (Absorbance) | 0.03 | 0.02 | 0.06 | 0.05 | 0.08 | 0.1 | 0.09 | 0.12 | 0.17 | 0.11 |
| Percent Transmission 430 nm / 659 nm (%) | 99.9 100.0 | 99.9 100.0 | 99.9 99.9 | 99.9 100.0 | 99.9 99.9 | 99.8 99.9 | 99.9 99.9 | 99.8 99.9 | 99.9 99.9 | 99.8 99.9 |
| Physical Test |  |  |  |  |  |  |  |  |  |  |
| Hardness JIS A Type (degree) | 44 | 41 | 41 | 42 | 42 | 43 | 44 | 40 | 41 | 44 |
| Liquid Leakage Test (ml) | 0.0 | 0.0 | 0.0 | 0.1 | 0.5 | 0.6 | 0.9 | 0.6 | 0.6 | 0.6 |
| Coring Test (released pieces / total number of needle piercing) | 0/40 | 0/40 | 0/40 | 1/40 | 5/40 | 9/40 | 13/40 | 7/40 | 6/40 | 10/40 |
| Estimation of Chemical Adaptability of Rubber Stopper | ◯ | ◯ | ◯ | ◯ | X | X | X | X | X | X |
| Estimation of Functionality of Rubber Stopper | ◎ | ◎ | ◎ | ◎ | X | X | X | X | X | X |

Advantages of Present Invention

In the rubber composition or the crosslinked product thereof according to the present invention, there can be obtained advantages by the simple construction to specify a density of at most 0.95 that the secondary crosslinking by radiation can be carried out with a lower dose and the radiation treatment is effectively advanced with less oxidation deterioration of the resin since radiation is readily transmitted. Further, distribution width of the dose distribution is so small that sterilization precision be maintained higher and in particular, when applying radiation to a fluoro resin-laminated crosslinked material or product, damage on the fluoro resin be decreased.

What is claimed is:

1. A rubber composition or its crosslinked product used for a rubber stopper for a medicament or a rubber article for a medical treatment, comprising an isobutylene copolymer, as a predominant component, which is at least one member selected from the group consisting of isobutylene-isoprene copolymers (IIR), chlorinated isobutylene-isoprene copolymers (C-IIR), brominated isobutylene-isoprene copolymers (B-IIR), crosslinked isobutylene-isoprene-divinylbenzene ternary copolymers (XL-IIR) and brominated isobutylenepara-methystyrene copolymers (BIMS), wherein the rubber composition or its crosslinked product has a density of at most 0.95, and can be readily subjected to a radiation treatment.

2. A method of treatment comprising applying a radiation to a rubber composition comprising an isobutylene copolymer, as a predominant component, which is at least one member selected from the group consisting of isobutylene-isoprene copolymers (IIR), chlorinated isobutylene-isoprene copolymers (C-IIR), brominated isobutylene-isoprene copolymers (B-IIR), crosslinked isobutylene-isoprene-divinylbenzene ternary copolymers (XL-IIR) and brominated isobutylene-para-methylstyrene copolymers (BIMS), wherein the rubber composition has a density of at most 0.95, and thereby carrying out crosslinking of said composition or sterilization of the crosslinked product thereof.

* * * * *